United States Patent [19]

Owen et al.

[11] Patent Number: 4,561,963

[45] Date of Patent: Dec. 31, 1985

[54] ANTIMONY AND GRAPHITE HYDROGEN ION ELECTRODE AND METHOD OF MAKING SUCH ELECTRODE

[75] Inventors: Jeffrey D. Owen; Harold M. Brown, both of Salt Lake City, Utah

[73] Assignee: Zinetics Medical Technology Corporation, Salt Lake City, Utah

[21] Appl. No.: 635,755

[22] Filed: Jul. 30, 1984

[51] Int. Cl.$^4$ .............................................. G01N 27/30
[52] U.S. Cl. ................................... 204/433; 128/635; 204/419; 204/435
[58] Field of Search ............... 204/433, 400, 1 H, 435, 204/294, 419; 128/635

[56] References Cited

U.S. PATENT DOCUMENTS

| | | | |
|---|---|---|---|
| 2,168,867 | 8/1939 | George | 204/433 X |
| 2,288,180 | 6/1942 | Brengman | 204/433 |
| 3,742,594 | 7/1973 | Kleinberg | 204/433 X |
| 4,109,648 | 8/1978 | Larke et al. | 128/639 |
| 4,119,498 | 10/1978 | Edwall et al. | 204/1 T |
| 4,221,567 | 9/1980 | Clark et al. | 23/230 B |
| 4,340,615 | 7/1982 | Goodwin et al. | 427/2 |
| 4,431,508 | 2/1984 | Brown et al. | 204/418 |

FOREIGN PATENT DOCUMENTS

122258  2/1972  Denmark ........................... 128/639

OTHER PUBLICATIONS

Alfred Uhl et al., Sitzungsberi Chte. d. Mattlem.-Natur w. dl., ABt., IIb 132, 29-34 (1923).
Howard W. Haggard, Science, pp. 479-480, vol. 93, May 16, 1941.
D. P. Shoemaker et al., "Electrodes For Electrochemical Cells, Experiments in Phys. Chem.", 4th Edit., pp. 693-695, (1981).
H. J. Bicher et al., J. Appl. Physiology, pp. 387-390.
MI-506 and 508 Flexible pH Electrode, Advertisement.
George Perley, Chem. & Metallurgical Engineering, pp. 417-420, vol. 40, No. 8, (1933).
M. Markdahl-Bjarme et al., Medical & Biological Engineering and Computing, pp. 447-456, Jul. 1981.
Sensors That Mate With Our Electro-Chem. Analyzer, Advertisement, Diamond Electro-Tech. Corp.
G. Edwall, Electrochimica Acta., vol. 24, pp. 595-603, (1979).
G. Edwall, Med. and Biol. Eng. and Comput., pp. 661-669, 16, (1978).
J. W. Brantigan et al., J. Appl, Physiology, vol. 40, No. 3, pp. 443-446, (1976).
Gerhard Malnic et al., Yale J. Biology & Med., vol. 45, No. 3-4, pp. 356-367, (1972).
H. J. Bicher et al., Biochem., Biophys. Acta., 255, pp. 900-904, (1972).
R. L. Coon et al., J. Appl. Physiology, vol. 40, No. 4, pp. 625-629, (1976).
O. H. LeBlanc et al., J. Appl. Physiology, vol. 10, No. 4, (1976).

(List continued on next page.)

*Primary Examiner*—G. L. Kaplan
*Attorney, Agent, or Firm*—Mallinckrodt, Mallinckrodt, Russell & Osburn

[57] ABSTRACT

A solid state electrode that includes a graphite core as both the internal reference and the electrical conductor that is preferably formed of graphite threads maintained as a bundle that in one embodiment, has an end thereof coated with a mixture of antimony and antimony oxide as a sensor element, the graphite junction forming the internal reference to that sensor element, and in another embodiment, the graphite core is wrapped tightly around a sensor formed from section or "shot" of a mixture antimony and antimony oxide, the graphite junction forming the internal reference thereto. The connected graphite core and antimony/antimony oxide sensor are then covered with an impermeable non-conductive plastic sheath, leaving a section of the antimony/antimony oxide sensor surface exposed, and the junction of that sheath to the antimony/antimony oxide sensor is preferably sealed as with an epoxy.

25 Claims, 5 Drawing Figures

OTHER PUBLICATIONS

Erling Nilsson, "Continuous Intra-Vascular Monitoring of pH and pO2", Royal Institute of Tech., (1983).
E. Nilsson et al., Scand. J. Clin. Lab. Invest., 41, 333–338, (1981).
E. Nilsson et al., Scand. J. Clin. Lab. Invest., 42, 323–329, (1982).
E. Nilsson et al., Scand. J. Clin. Lab. Invest., 41, 557–563, (1981).
E. Nilsson et al., Scand. J. Clin. Lab. Invest., 42, 331–338, (1982).
Evaluation of Intragastric pH in Acutely Ill Patients by Virginia Herrmann, M.D. and Donald L. Kaminski, M.D., Arch. Surg.—vol. 114, Apr. 1979.
Preliminary Report on a New Method for Gastric Research by Russell C. Erb and Kenneth L. Senior, Journal A.O.A., pp. 95–96, Oct., 1938.
The Antimony–Antimony Oxide Electrode, by John T. Stock, William C. Purdy and Lucinda M. Garcia, Jan. 31, 1958.

stressed, but its importance as a standard internal reference system was not described. Whereas, the present invention utilizes untreated graphite both as the conductor and as the internal reference at the junction of that graphite to an antimony sensor. In addition, production of the Kleinburg electrode requires precision soldering of the antimony micro-rods to a silver wire.

Recently it was determined that the design of Kleinberg could be further improved by using elaborately prepared single crystals of antimony or monocrystalline antimony, N. E. G. Edwall and G. S. Eklund "Monocrystalline Metal Electrode and Method of Use", U. S. Pat. No. 4,119,498; 1978. Production of this Edwall electrode however requires extremely precise measurements and manipulations of monocrystalline antimony, and minor flaws in the antimony crystal structure will cause the electrode to inaccurately sense changes in pH. Such electrode is therefore very labor intensive and is extremely expensive to produce.

The accuracy and stability of antimony electrodes generally has been attributed to the stability of a defined internal reference system that involves a reversible electrochemical system based on well established reduction-oxidation principles. Such has been detailed in, J. Ruzicka and C. G. Lamm, "Electrode for Potentiometric Measurements", U.S. Pat. No. 3,926,765; 1975. This patent teaches an electrochemically active redox system that is sensitive to ions in solution, and a humid, solid, water soluble compound which acts as a carrier for this redox system. The importance of this internal reference system was demonstrated in Kleinberg by a substitution of a silver for a copper wire, which substitutuion resulted in an extremely stable electrode.

Antimony pH electrodes that utilize a standard internal reference system are commercially available. One such antimony pH electrode is marketed by Diamond Electro-Tech Inc., (Ann Arbor, MI) and is available in either a miniature tip size (1 mm diameter) or a micro tip size (80 $\mu$m diameter). Unlike the present invention, each of these electrodes use a silver wire as the standard internal reference electrode system. Another antimony pH electrode is commercially available from Harco Electronic, Ltd. (Winnipeg, Manitoba, Canada). This electrode also utilizes silver as the inernal reference system and includes epoxy to seal the micro crevices between a plastic sheath and the antimony that is similar to the electrode taught in, I. Kleinberg, "Antimony electrodes and Methods of Manufacturing Same", U.S. Pat. No. 3,742,594; 1973.

Where other pH electrodes have used materials other than antimony for the pH sensor, such have consistantly taught the use of silver as the material of a standard internal reference junction therewith. For example, the metal palladium (Pd) will respond to pH changes and has been used as an electrode sensor element. Such palladium electrodes have used an internal reference junction made of silver. This is set out in, R. L. Coon, N. C. J. Lai and J. P. Kampine, "Evaluation of a Dual-Function pH and $pCO_2$ In-Vivo Sensor", *J. Appl. Physiol.* 40: 625–629, 1976. Another type of pH sensor that includes a non-metal embedded in plastic and uses silver as the internal reference system is set out in, O. H. LeBlanc, Jr., J. F. Brown, Jr., J. F. Klebe, L. W. Niedrach, G. M. J. Sluxarczuk and W. H. Stoddard, Jr., "Polymer Membrane Sensors for Continuous Intravascular Monitoring of Blood pH", *J. Appl. Physiol.* 40, 644–647, 1976. A more recent reference that teaches a use of silver in conjunction with one of its salts or the reduced metal salt (e.g. silver black) to produce a stable electrode system is set out in, J. A. R. Kater, "Ion-Selective Electrodes", U.S. Pat. No. 4,340,457; 1982. This patent teaches adding silver black and platinum black to a standard internal reference system, like that set out in Ruzicka, and is employed in order toenhance electrode stability.

An exception to the above wherein is taught a use of a well-defined standard internal reference electrode system is shown in FIG. 5 of a patent by, I. Binder and H. A. Teass, Jr., "An All Solid State Electrode System", U.S. Pat. No. 4,338,175; 1982. It is, however, not possible to evaluate the preferred internal reference system from the description given in this patent. Unlike the present invention however, the electrode system of this patent is configured for use in mining and mineral processing and the electrode system itself is contructed of two electrodes; one made of a noble metal that functions as the reference electrode, with the other made of ultra-pure antimony that is sensitive to fluctuations in ion levels in a solution whose ph is to be measured. This electrode is very expensive to construct as the antimony must be ultra-pure (99.999% antimony), as a less pure grade will not give stable and reproducible pH readings. Application of this arrangement as an indwelling pH electrode is therefore not practical due to its complexity and its use of expensive metals.

The present inventors have used graphite in an ion-sensitive electrode as an internal reference system when that graphite is appropriately chemically treated with a coating of a silanizing agent, H. M. Brown, Jr. and J. D. Owen, "Solid State Graphite Electrode", U.S. Pat. No. 4,431,508; 1984. This patent, however, does not teach, as does the present invention that graphite which has not been chemically or physically altered will form a stable internal reference system when coupled with a metal pH sensor, that is preferably an antimony/antimony oxide section.

The present invention differs from the above-cited references and patents, as set out above, in a number of significant ways. It does not require a labor-intensive mono-crystalline antimony manipulation. Instead its practice can involve a number of different forms of polycrystalline antimony that are easily mixed together and are preferably joined either during or after that mixing process to a body formed of untreated graphite fibers that are joined in a bundle, the graphite at the junction functioning as an internal reference system. The electrode of the present invention, therefore, does not require a use of silver for either connection between an antimony sensor and an electrical lead, as do a number of the earlier electrodes. The electrode of the present invention can be used conveniently in conjunction with a standard potentiometer and a standard electrocardiogram (E.K.G.) lead which forms the external reference electrode. The electrodes can be designed for minimal patient discomfort, are inexpensive to construct, and are disposable. Also, the electrode of the present invention requires no pre-calibration, thereby reducing labor costs associated with measuring stomach fluid pH, making it far less expensive to produce and to use than earlier antimony electrodes.

SUMMARY OF THE INVENTION

It is, therefore, a general objective of the present invention to provide a solid state electrode that is suitable for measuring a patient's stomach fluid pH.

ANTIMONY AND GRAPHITE HYDROGEN ION ELECTRODE AND METHOD OF MAKING SUCH ELECTRODE

BACKGROUND OF THE INVENTION

1. Field of the Invention

This invention relates to electrodes for use in measuring hydrogen ion concentration that use antimony as the electrode's sensing element, and in particular it relates to pH electrodes for measuring acidity in stomach fluids.

2. History of The Invention

The present invention involves a solid state electrochemically ion-selective electrode system preferably for measuring the pH of solutions, especially stomach fluids, and it relates to using untreated graphite and a pH sensing material (graphite/metal) as a novel internal reference electrode system.

There is a long-felt need in the health care industry for a relatively inexpensive and yet stable electrode for accurately measuring the hydrogen ion concentration, or pH, of stomach secretions. This is especially relevant in the care of acutely ill or traumatized patients who frequently die from bleeding gastric ulcers produced by stress. These ulcers are the result of an abnormally high concentration of hydrogen ions in the stomach fluid, and may be diagnosed from the presence of a low pH. Such patients' stomach pH should therefore be monitored continuously over a period of several days in order that their ulcers may be controlled by effective medication. Unfortunately, such monitoring has not heretofore been practical due to the pH electrodes that have been available. An electrode to effectively meet patient needs should: be small and flexible enough to be inserted with minimal patient discomfort; give a stable pH reading over a period of three to four days; and be inexpensive to construct. A need for such an electrode is clearly demonstrated from an examination of current methods of bleeding ulcer treatment.

Ulcer treatment has generally been based on raising the pH of the stomach fluids through the use of antacids. Antacids are administered when stomach fluid samples, taken periodically, become too acidic.

There are currently three methods of measuring gastric pH:

(1) Electrochemically by a pH electrode placed in aspirated stomach fluid;
(2) Visual color matching of litmus paper, exposed to aspirated stomach fluid;
(3) Electrochemically by an indwelling stomach pH electrode.

The first two techniques do not provide instant information or "real-time" data for the physician, as they must be taken after the stomach fluid has been removed and are costly due to the labor involved in acquiring a fresh sample of stomach fluid for each measurement.

An alternative to frequent stomach fluid sampling has been to administer cimetidine, a substance which prevents the histamine induced release of acid into the stomach as set out in R. Herrmann and D. L. Kaminski, "Evaluation of Intragastic pH in Acutely Ill Patients", *Arch. Surg.* 14, 511–514, 1979. Currently in such treatment, there is no satisfactory method of monitoring pH which will give physicians immediate data on the patient's response to the cimetidine. Cimetidine is administered until there is an indication from periodic stomach samples that bleeding has stopped. As a result, the patient may be receiving insufficient or excess amounts of cimetidine. One problem with this line of treatment is that there is insufficient experimental evidence available to describe possible side-effects from over-administration of cimetidine. Finally, the cost of administering cimetidine is currently about twice as high as conventional antacid treatment, and therefore determination of minimum effective levels through immediate response monitoring as is provided by the present invention would benefit the cost of patient care as well as preventing possibly unknown side-effects.

A third method of monitoring gastric fluid pH is direct measurement with an indwelling pH electrode that will give the physician an immediate accurate reading of pH values. With this procedure, various modes of treatments can be assessed rapidly and safe dosage levels can be established with accuracy. Two main types of indwelling pH electrodes that are currently in use are constructed of either glass or antimony. Current glass pH electrodes appropriate for gastric analysis, are fragile and expensive to produce and transport. Such electrodes exhibit a high electrical resistance resulting in a protracted time response. A general discussion of some earlier antimony electrodes for measuring the acidity of stomach secretions is set out in: Erb, R. C., and Senior, K. L.: *J. Am. Osteopath. Assoc.* 38, 95, 1938; and Haggard, H. W., and Greenberg, L. A.: *Science* 93, 479, 1941.

3. Prior Art:

The use of an antimony electrode as a pH sensor was first reported in 1923, A. Uhl and W. Krestanek, "Die Elektrometrische Titration Vonsauren and Basen mit der Antimon-indikatorelektrode", *Sitzungsberichte d. mathem.-naturw. dl., Abt. IIb,* 132, 29, 1923. As set out therefore, electrodes were made of an antimony sensor connected directly to a copper wire, and the electrode was enclosed in a glass tube except for the exposed antimony sensor. This basic design has been reviewed in J. T. Stock, W. C. Purdy and L. M. Garcia, "The Antimony-Antimony Oxide Electrode", *Chem. Rev.* 58, 611–626, 1958. These electrodes remained essentially unchanged for a considerable time despite their inherent instability. A microelectrode version thereof has been described in, G. Malnic and F. L. Vieira, "The Antimony Microelectrode in Kidney Micropuncture", *Yale J. Biol. Med.* 45, 356–367, 1972.

More recently, several improvements in antimony electrodes have been reported that yield more stable results. One such electrode involves an antimony microelectrode that utilizes a silver/silver chloride internal reference system that was described in H. I. Bicher and S. Ohki, "Intracellular pH Electrode Experiments on the Giant Squid Axon" *Biochim. Biophys. Acta* 255, 900–904, 1972. This electrode consists of a glass tube containing an exposed antimony electrochemically connected to a silver/silver chloride wire by a solution of potassium chloride.

I. Kleinberg in, "Antimony electrodes and Methods of Manufacturing Same," U.S. Pat. No. 3,742,594, 1973, sets out the importance of using epoxy instead of glass to electrically insulate an antimony sensor from an electrical lead. The patent recognizes the antimony contains micro crevices, and these crevices are though to produce channels for water and electrolytes and thereby short-circuit the electrical potential changes that are due to a change in pH. Therein, the use of a silver wire between the antimony and a copper electrical lead was trodes. Such slow cooling of the molten antimony will promote large crystal growth which enhances the stability of the pH electrode, as set out in G. Edwall, "Influence of Crystallographic Properties on Antimony Electrode Potential I. Polycrystalline Material," *Electrochim. Acta* 24, 595–603, 1979.

FIG. 1 shows a side elevation sectional view of a first embodiment of an antimony and graphite hydrogen ion electrode 10 of the present invention hereinafter referred to as electrode 10. Electrode 10 is preferably constructed by tightly wrapping a "bundle" of untreated graphite threads 11 around a section, "shot" or rod of antimony/antimony oxide 12 that is untreated and is covered with impermeable plastic sheath 13 such as one formed from a polyvinylchloride (PVC) plastic that can be heat shrunk thereto, so as to leave exposed an antimony/antimony oxide tip end 14.

In FIG. 2 is shown a side elevation sectional view of an alternate or second embodiment of the antimony and graphite hydrogen ion electrode 20 of the present invention, hereinafter referred to as electrode 20. Electrode 20 also incorporates untreated graphite threads 21 but involves dipping or otherwise coating an end thereof with a molten mixture of antimony/antimony oxide 22, which coating and the threads above the coating are then covered with an impermeable plastic sheath 23 that is also preferably polyvinylchloride (PVC) so as to leave exposed an antimony/antimony oxide tip end 24. The electrodes 10 and 20 are each capable of accurately measuring hydrogen ion concentrations or pH of aqueous solutions. In each electrode the graphite at the junction with the antimony/antimony oxide sensor functions as an internal reference, with the graphite thereabove functioning as a conductor. Therefore, it should be understood that that portion of the graphite that functions as a conductor could be replaced with another electrically conductive material such as a copper wire, or the like, within the scope of this disclosure. Either electrode 10 or 20, when connected between a patient's body, that functions as an external reference electrode, and a potentiometer or like voltage measuring device, will continue to provide an accurate measurement of solution pH over a period of a number of days as will be discussed hereinafter with respect to FIGS. 3 through 5, allowing the electrode to remain within a patient's stomach over the period of an average patient hospital stay, which period, in practice, is three to four days.

Both the electrode 10 and 20 of FIGS. 1 and 2 preferably include encasing the electrode in a sheath of an impermeable plastic tubing 13 and 23 to cover the graphite/antimony junction so as to leave the antimony/antimony oxide tip end 14 or 24 exposed, and each electrode preferably includes an epoxy seal, shown at 15 in FIG. 1 and 25 in FIG. 2, that is coated around the junction of the sheath with the antimony tip edge to provide a moisture tight barrier or seal between the plastic sheath and that antimony/antimony oxide electrode tip. So arranged, each antimony/antimony oxide tip end 14 or 24 will be exposed to allow it to directly contact a solution whose pH is to be measured. The electrodes 10 and 20 are preferably encased by plastic sheath 13 and 23 over their length, with ends 16 and 26 thereof, respectively, of each connected to a conductive wire 17 of 27, or the like, that is, in turn, connected to a potentiometer, or like voltage potential measuring device, not shown.

A preferred method of constructing the electrode 10 of FIG 1, involves drawing molten antimony/antimony oxide heated to a molten state into a thin glass capillary tube, a preferred tube measuring approximately 1.7×100 mm., and allowing that mixture to slowly cool until solid. Antimony segments or rods are then obtained by breaking the glass tubes from therearound. The metal rods are then themselves broken into individual cyclindrical sections or "shots" and are in turn, connected to the graphite fibers by wrapping the fibers tightly around the rod section so as to form the graphite-antimony/antimony oxide interface. The preferred graphite is the Hercules Magnamite ® identified above, that is formed as a thread or bundle from approximately one thousand (1,000) graphite fibers, each fiber being approximately seven microns ($7 \times 10^{-6}$ meters) in diameter. Preferably, a bundle of 1000 of these graphite fibers is used for each electrode. After the antimony/antimony oxide tip is secured thereto, the bundle is covered with a tubular section of polyvinyl chloride (PVC) heat-shrink plastic tubing that is heated to shrink to the bundle, forming an electrical insulator thereover, while leaving an antimony/antimony oxide tip end surface uncovered. Thereafter, an epoxy is preferably applied between the exposed antimony/antimony oxide tip end edges junction with the tubing inner circumference forming a moisture proof seal. The opposite end off the electrode is then ready for connection to a conductive lead that, in turn, is connected to a potentiometer, or like electrical potential measuring device. The potentiometer is also connected by a separate line, such as a standard electrocardiogram (E.K.G) lead, to the patient's skin, the patient functioning in the loop as an external reference electrode. Such E.K.G. leads are specially designed for minimal patient discomfort, are relatively inexpensive and are disposable. The electrode so formed has been found in practice to work without preconditioning, to provide an accurate measure of the presence of hydrogen ions in solution.

Another preferred construction procedure used to produce the electrode 20, includes a utilization of elemental powdered antimony that is obtained in bulk. This powdered antimony as in the fabrication of the electrode 10 of FIG. 1, is heated to melting in a ceramic beaker to approximately 700° Celsius, and that temperature is maintained, (the melting temperature of antimony is 630.74° Celsius) thus forming a mixture of antimony (Sb) and antimony oxide ($SbO_3$). The presence of antimony oxide ($SbO_3$) is necessary to provide an effective sensor tip for accurately sensing hydrogen ion concentration and passing that sensed concentration, as a voltage potential, across the internal reference junction of the sensor tip into the contacting graphite. After melting, the antimony/antimony oxide mixture is used to construct the electrode of FIG. 2, by dipping the untreated graphite bundle end directly into the molten antimony/antimony oxide, removing that end therefrom, and allowing the antimony/antimony oxide that remains thereon to cool and harden. Usually one dipping of the bundle of fibers in the molten antimony/antimony oxide mixture will provide a sufficient coating that, when it is allowed to cool and solidify, will produce a very thin layer of antimony/antimony oxide bonded to the graphite fibers. Thereafter the bundle is encased within the plastic tubing 23, leaving an antimony/antimony oxide end 24 surface exposed, and any space between the edge of that end and the plastic It is another objective of the invention to provide an indwelling antimony pH stomach fluid electrode which uses a graphite/metal junction as an internal reference system.

It is another objective of the invention is to provide an electrode which is extremely flexible to minimize discomfort when it is inserted into the patient's stomach.

It is another objective of the invention to provide a stable solid state electrode that will accurately monitor the pH of stomach fluids over a test period of a number of days of an average hospital stay.

It is still another objective of the invention to provide a solid-state electrode which does not require calibration prior to use.

It is still another objective of the invention to provide an electrode which can be easily and inexpensively constructed.

In accordance with the above objectives, the present invention is in an indwelling electrode for measuring stomach fluid pH that consists of an antimony sensor that is connected directly to a bundle of graphite fibers. The graphite/metal junction provides the electrode internal reference. The assembly is then electrically insulated except for an exposed end surface of the antimony sensor, as by a plastic sheath or tube shrunk fit thereover and may include an epoxy seal therebetween.

The electrode is preferably formed to have a small diameter facilitating its insertion with minimal patient discomfort into a patient's stomach. Without conditioning, the electrode will measure as an internal reference electrode a change in hydrogen ion concentration reflective of a pH change as an electrical potential which potential is sensed across the antimony and graphite junction and registers at a monitoring device. The electrode is connected between a patient's body that functions as an external reference for the electrode, and a voltage measuring device. So arranged the electrode will faithfully sense and transmit to the voltage measuring device a voltage presence over a test period of a number of days that is the average patient hospital stay. In practice, when maintained in a solution of known pH simulating a patient's stomach fluid, an embodiment of the invention continued to give a stable pH reading even after several days.

BRIEF DESCRIPTION OF THE DRAWINGS

These and other objects will appear in the following detailed description in which preferred embodiments have been described in detail in conjunction with the accompanying drawings.

DETAILED DESCRIPTION

Figure 1:
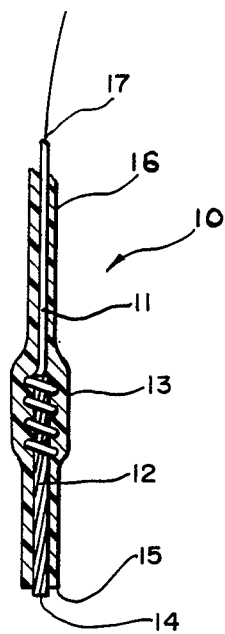
FIG. 1 is a side elevation sectional view of a first embodiment of an antimony and graphite electrode of the present invention.

Referring now to the drawings:

Earlier electrodes appropriate for sensing hydrogen ion concentration have generally involved a solid electrochemically active redox system to produce a stable electrode potential. Such a redox system has typically been a mercury and mercury chloride (calomel), or silver and silver chloride. The electrode of the present invention does not require such internal redox system, and in fact, employs only a section of an untreated graphite that is in contact and forms an electrically conductive junction with a sensor of antimony (Sb), functioning as an internal reference for the electrode.

Figure 2:
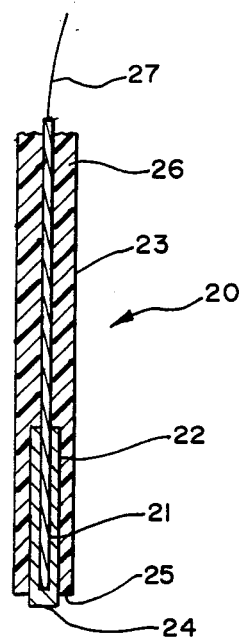
FIG. 2 is a side elevation sectional view of a second embodiment of an antimony and graphite electrode of the present invention.

The basic electrode of the present invention is illustrated in FIGS. 1 and 2 as consisting of a bundle of untreated graphite threads that are wrapped around or otherwise connected to a cylindrical section of piece of antimony/antimony oxide. The antimony/graphite junction that forms the internal reference for the electrode is then covered by shrink fitting a plastic sheath thereto that can then be sealed as with an epoxy arranged between the antimony end edge and sheath wall to seal out moisture while leaving the antimony face exposed. So arranged, the antimony/antimony oxide section will function as the sensing element, the graphite at the graphite/antimony junction acting as the internal reference system with the untreated graphite above this junction functioning as a flexible electrical conductor.

The preferred untreated graphite and antimony/antimony oxide used in the construction of the electrode are inexpensive. The antimony used to manufacture the antimony/antimony oxide sensor need only be technical grade, which costs about a penny per electrode, and the preferred graphite will cost about two cents per foot. In practice a graphite manufactured by Hercules Corporation's known as Magnamite ® has been found to work satisfactorily and consists of a thin flexible bundle of graphite fibers, the bundle containing approximately one thousand individual thin graphite fibers maintained together. The small diameter of the bundle facilitiates its insertion, with minimal discomfort or harm, through a patient's throat and into their stomach. The graphite fibers in each bundle are small; (approximately seven microns $7 \times 10^{-6}$ meters) in diameter and when wrapped together form as the bundle a small thread of graphite that has a tensile strength of about 400,000 pounds per square inch. This is approximately twenty times the tensile strength of a copper wire of the same diameter. The electrode has a long storage life and can be taken off the shelf and used immediately without conditioning, special treatment or preparation. In addition, calibration of the electrode is generally unnecessary as all electrodes that are of similar construction, will provide a measure of pH accurate to within ±0.5 pH units which is more than sufficient accuracy for intragastric measurements.

A preferred method of electrode construction involves drawing molten antimony/antimony oxide into a thin glass capilliary tube of a diameter of approximatley $1.7 \times 100$ mm, and allowing it to slowly cool until solid. The glass capilliary is then broken away from the brittle antimony oxide rod, which itself can then be easily broken into smaller pieces to make individual electubing inner circumference is sealed at 25 by application of an epoxy, or the like, thereto.

The graphite/antimony interface of electrode 20 like that of electrode 10, will function as an internal reference, passing an electrode potential to a voltage measuring device that remains consistent over a significant time period. The antimony electrode potential can be referred to as a corrosion potential, and, although it is not thoroughly understood, it is believed to be mainly governed by the following two equations as set out in, M. Markdahl-Bjarme and G. Edwall, "Modified Conventional Type of pCO$_2$-Electrode With Monocrystalline Antimony as the pH-sensing Element", *Med Biol. Eng. Comput.* 19, 447–456, 1981.

$$2Sb + 3H_2O \rightleftharpoons Sb_2O_3 + 6H^+ + 6e^-$$

and

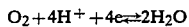

$$O_2 + 4H^+ + 4e \rightleftharpoons 2H_2O$$

Figure 3:
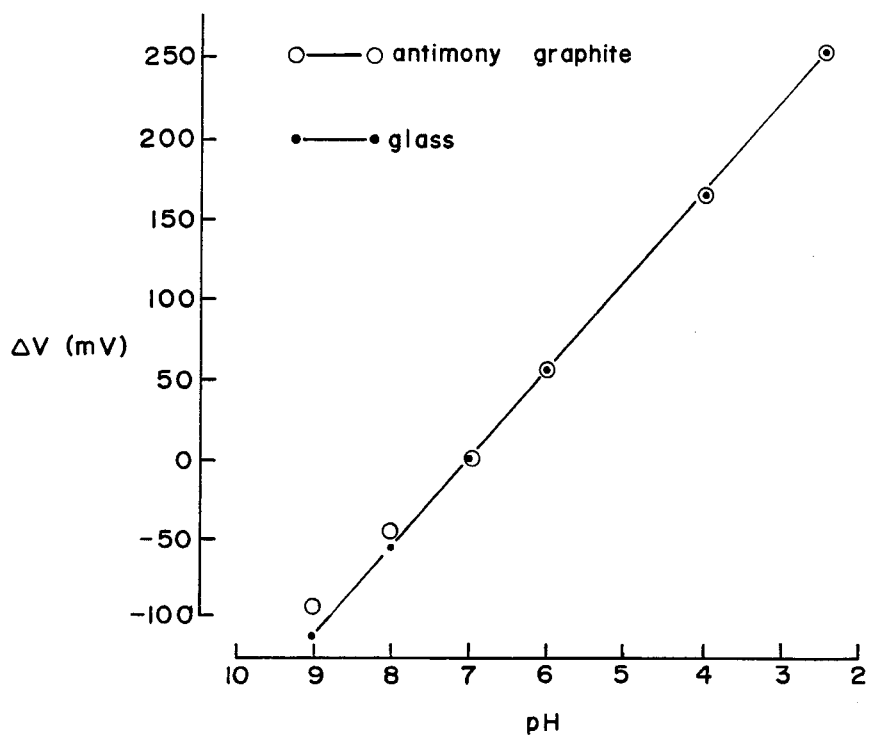
FIG. 3 is a graph comparing pH readings of the antimony electrode of the present invention with those of a conventional glass electrode in the same solutions, demonstrating the ability of the present invention to accurately measure pH over a broad range.

That the graphite/antimony electrode will perform as a pH electrode is demonstrated in FIG. 3. Therein, the open circles (o) show the change in potential (mV) of a graphite/antimony electrode as compared with a change in potential measured by a conventional glass pH electrode in the same solution identified as closed circles (o).

Figure 4:
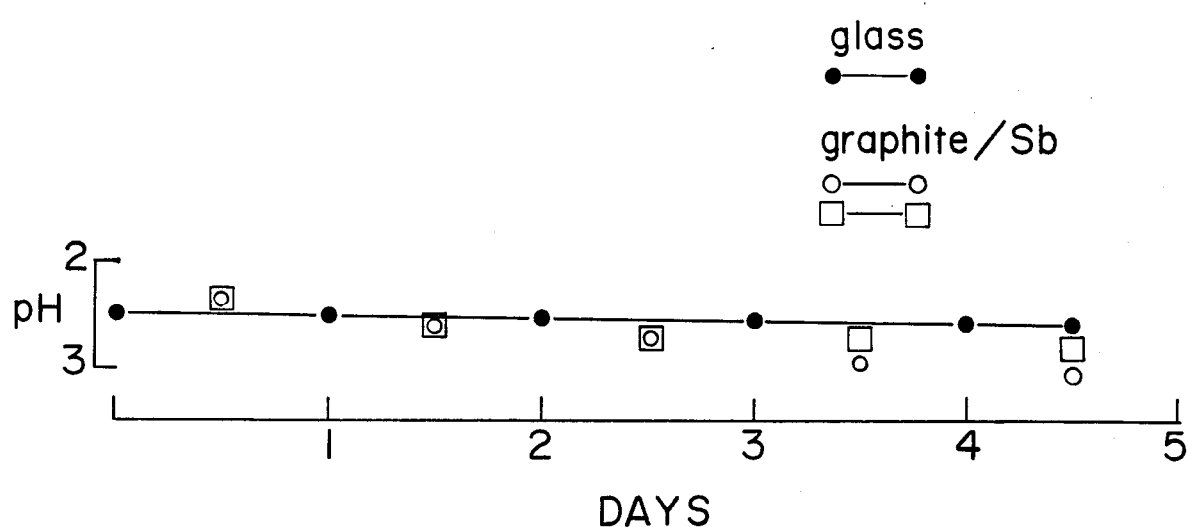
FIG. 4 is a graph comparing pH readings of antimony electrodes of the present invention maintained in the same solutions with a conventional glass electrode, demonstrating the reliability of the antimony electrode over a period of several days.

In FIG. 4 the long-term stability of two separate graphite/antimony electrodes is compared with that of a standard glass pH electrode. The graph shows that, over a period of two and one-half days, the apparent pH of the graphite-antimony electrodes was identical and only a difference of 0.2 pH unit was seen after four and one half days, with the glass pH electrode shown to have drifted about 0.1 pH unit over that four and one-half day period.

Figure 5:
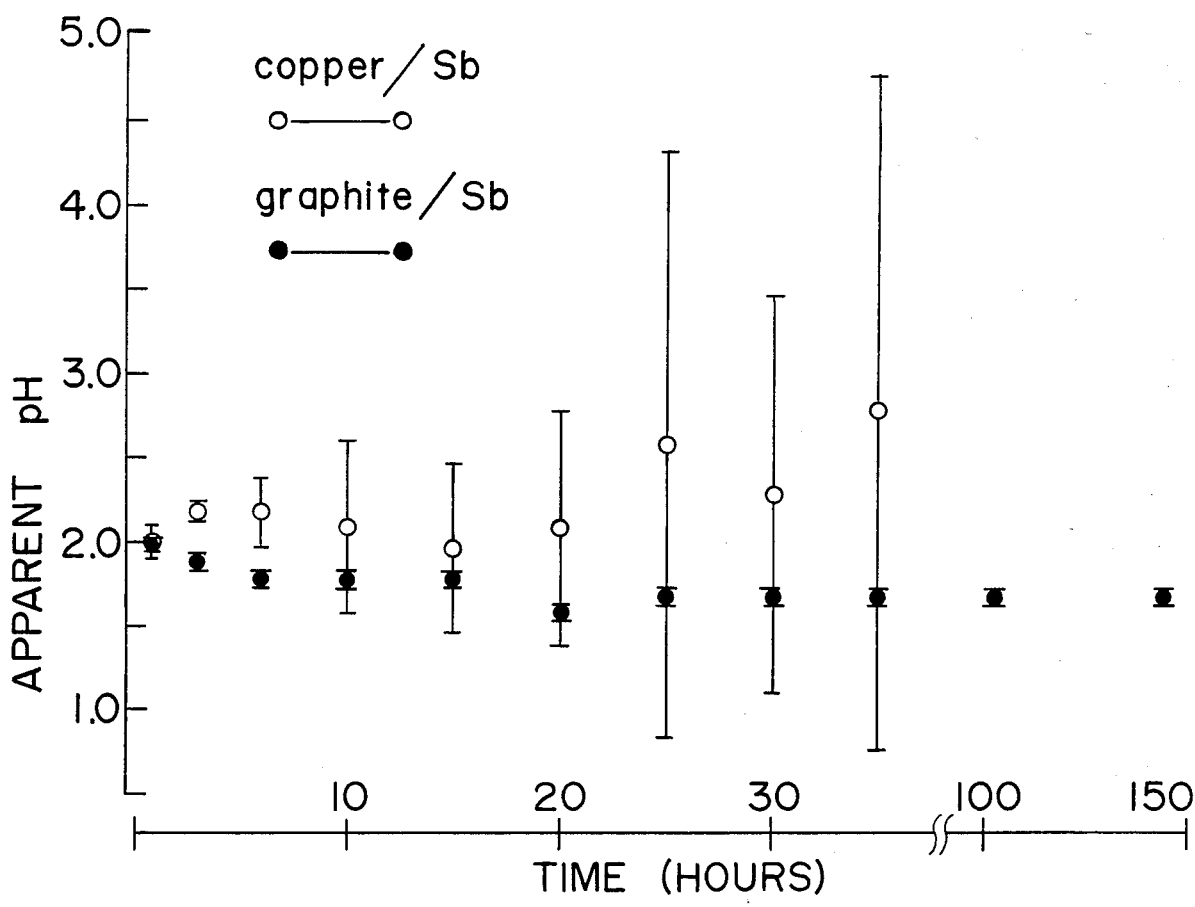
FIG. 5 is a graph comparing the antimony electrode of the present invention with a copper/antimony electrode in the same solution over time.

FIG. 5 shows vertical lines bisecting open (o) and closed (●) circles that indicate, respectively, copper/antimony and graphite/antimony electrodes, the length of the vertical lines indicating the variance in pH values obtained from three individual antimony/graphite electrodes as compared to equivalent data from electrodes with antimony/copper junctions, utilizing a pH 2 solution. The data was obtained over 150 hours of recording. The bars represent the standard deviation, with a range of acceptable error for gastric analysis, of ±0.5 pH unit. From an inspection of FIG. 5, the antimony/graphite electrodes showed a small drift of about −0.25 pH unit for the initial 10 hours, with an apparent change of only 0.05 pH unit during the period from 25–150 hours, that is well within the range of acceptable error whereas, the copper/antimony electrodes are shown to have drifted appreciably at the 10 hour point and continued to drift badly thereafter. It is obvious from FIG. 5 that the standard deviation of readings from the antimony/graphite electrode of any single data point is very "tight" compared to the readings from the copper/antimony electrodes. In practice and as has been set out in the earlier cited patent by N. E. G. Edwall, and G. S. Eklund, "Monocrystalline Metal Electrode and Method of Use", U.S. Pat. No. 4,119,498; 1978, the characteristics of low drift and small standard deviation can be further enhanced by a slower cooling of the antimony in a practice of fabricating the electrode of the present invention.

While hereinabove have been detailed preferred embodiments of antimony/antimony electrodes and a process for their manufacture, it should be understood that the electrode of the invention can be formed by processes different from those described and that other configurations or arrangements of untreated graphite and even different types of untreated graphite can be used from those set out herein within the scope of this disclosure so long as the graphite/antimony junction is "tight" to produce the required internal reference junction. It should, therefore, be understood that the present disclosure is made by way of example only and that changes in the electrode construction from the preferred embodiments and in the outlined processes of manufacture, can be made without departing from the subject matter coming within the scope of the following claims, which claims we regard as our invention.

We claim:

1. An electrode for use in measuring hydrogen ion concentration comprising, a graphite core; an antimony/antimony oxide sensor secured in electrical contact with said graphite core and having an exposed surface for immersion in a test solution; and means for electrically isolating said graphite core and antimony/antimony oxide sensor junction from said test solution when said antimony/antimony oxide exposed surface is immersed therein.

2. An electrode according to claim 1, wherein the means for electrically isolating said graphite core consists of an impermeable plastic coating arranged over said graphite core and over said antimony/antimony oxide sensor junction to said graphite core, so as to leave a surface of said sensor exposed.

3. An electrode according to claim 2, wherein the impermeable plastic coating is a tubular plastic sheath that is fitted over and shrunk to closely fit against the graphite core and graphite and antimony/antimony oxide sensor junction.

4. An electrode according to claim 3, wherein the impermeable plastic sheath is heat-shrink polyvinylchoride (PCV) plastic.

5. An electrode according to claim 2 further including an epoxy seal arranged as a moisture proof seal between the tubular plastic sheath inner circumference and the edge of the antimony/antimony oxide exposed surface.

6. An electrode according to claim 1, wherein the untreated graphite core is a bundle of flexible graphite fibers maintained together.

7. An electrode according to claim 6, wherein the antimony/antimony oxide sensor surface is formed by dipping the end of the bundle of graphite fibers into molten antimony/antimony oxide to coat the fibers with that antimony/antimony oxide and allowing that coating to dry thereto.

8. An electrode according to claim 1, wherein the antimony/antimony sensor consists of, a solid section of antimony/antimony oxide that receives the graphite core wrapped therearound forming an electrical junction where said section of antimony/antimony oxide is contacted by said graphite core.

9. An electrode according to claim 1, wherein the mix of antimony and antimony oxide is obtained by heating elemental powdered antimony to approximately 700° Celsius.

10. An electrode for use in measuring hydrogen ion concentration comprising, an antimony/antimony oxide sensor; a section of graphite maintained in electrical contact to said antimony/antimony oxide sensor functioning as an internal reference; electrically conductive means connected to said section of graphite for passing an electrical potential therefrom; and means for electrically isolating said section of graphite and connected electrically conductive means from a test solution to leave exposed a portion of said antimony/antimony oxide sensor to said test solution.

11. An electrode according to claim 10, wherein the means for electrically isolating said section of graphite and electically conductive means consists of an impermeable plastic coating arranged over said section of graphite, the electrically conductive means and over said antimony/antimony oxide sensor junction to said section of graphite, so as to leave a surface of said sensor exposed.

12. An electrode according to claim 11, wherein the impermeable plastic coating is a tubular plastic sheath that is fitted over and shrunk to closely fit there against.

13. An electrode according to claim 12, wherein the impermeable plastic sheath is heat-shrink polyvinylchloride (PVC) plastic.

14. An electrode according to claim 11, further including an epoxy seal arranged as a moisture proof seal between the tubular plastic sheath inner circumference and the edge of the antimony/antimony oxide exposed surface.

15. An electrode according to claim 10, wherein the section of graphite and the electrically conductive means is a bundle of flexible graphite fibers maintained together.

16. An electrode according to claim 15, wherein the section of graphite junction with the antimony/antimony oxide sensor surface is formed by dipping the end of the bundle of graphite fibers into molten antimony/antimony oxide to coat the fibers with that antimony/antimony oxide and allowing that coating to dry thereto.

17. An electrode according to claim 15, wherein the section of graphite junction with the antimony/antimony oxide sensor is formed by wrapping the bundle of graphite fibers around a solid section of antimony/antimony oxide so as to form an electrical junction, while leaving an antimony/antimony oxide surface exposed.

18. An electrode according to claim 10, wherein the mix of antimony and antimony oxide is obtained by heating elemental powdered antimony to approximately 700° Celsius.

19. A process for manufacturing an antimony and graphite hydrogen ion electrode comprising the steps of, connecting a section of graphite to an antimony/antimony oxide sensor so as to provide an internal reference junction; connecting that section of graphite to an electrical conductor; encasing said graphite and antimony/antimony oxide sensor junction and the electrical conductor in a liquid impervious sheath so as to leave a portion of said sensor exposed; and connecting said electrical conductor to an electrically conductive lead.

20. A process of manufacture as recited in claim 19, wherein the section of graphite and the electrical conductor is a bundle of graphite fibers consisting of approximately one thousand fibers each of an average diameter of seven (7) microns.

21. A process of manufacture as recited in claim 19, further including the step of applying an epoxy as a liquid tight seal between the sheath and the adjacent antimony/antimony oxide sensor edge providing a liquid tight seal around the junction of the antimony/antimony oxide and section of graphite.

22. A process of manufacture as recited in claim 19, wherein the antimony/antimony oxide sensor is formed by drawing a column of a molten mix of antimony/antimony oxide into a breakable tube; allowing said mix to cool; breaking said tube away therefrom and breaking the solidified column into sections or "shots"; and wrapping the graphite bundle therearound to form the internal reference junction therebetween.

23. A process of manufacture as recited in claim 22, wherein the molten antimony/antimony oxide mix is allowed to cool in atmosphere.

24. A process of manufacture as recited in claim 19, wherein the antimony/antimony oxide sensor is formed by dipping an end of the untreated graphite bundle into a molten mix of antimony/antimony oxide; withdrawing that dipped end; and allowing the antimony/antimony oxide mix to dry and solidify thereon.

25. A process of manufacture as recited in claim 19, further including the step of connecting an electrically conductive lead to the graphite above the graphite-antimony/antimony oxide junction.

* * * * *